United States Patent
Mallipeddi et al.

(10) Patent No.: US 9,486,530 B1
(45) Date of Patent: Nov. 8, 2016

(54) GANCICLOVIR COMPOSITIONS AND RELATED METHODS

(71) Applicants: Sreerama Murthy Mallipeddi, Hickory, NC (US); Jonathan E. Sterling, Morganton, NC (US); Phanesh B. Koneru, Ashburn, VA (US)

(72) Inventors: Sreerama Murthy Mallipeddi, Hickory, NC (US); Jonathan E. Sterling, Morganton, NC (US); Phanesh B. Koneru, Ashburn, VA (US)

(73) Assignee: Exela Pharma Sciences, LLC, Ashburn, VA (US)

(*) Notice: Subject to any disclaimer, the term of this patent is extended or adjusted under 35 U.S.C. 154(b) by 0 days.

(21) Appl. No.: 14/475,206

(22) Filed: Sep. 2, 2014

Related U.S. Application Data

(60) Provisional application No. 61/872,625, filed on Aug. 30, 2013.

(51) Int. Cl.
*A61K 31/522* (2006.01)
*A61K 47/26* (2006.01)
*A61K 47/02* (2006.01)

(52) U.S. Cl.
CPC ............ *A61K 47/26* (2013.01); *A61K 31/522* (2013.01); *A61K 47/02* (2013.01)

(58) Field of Classification Search
CPC ..... A61K 47/02; A61K 47/26; A61K 31/522
See application file for complete search history.

(56) References Cited

U.S. PATENT DOCUMENTS 4,355,032 A 10/1982 Verheyden et al.

FOREIGN PATENT DOCUMENTS

| CN | 1626090 A | * | 6/2005 | ........... A61K 31/522 |
| CN | 1814275 A | * | 8/2006 | ............. A61K 38/00 |
| CN | 1868449 A | * | 11/2006 | ............... A61K 9/00 |

OTHER PUBLICATIONS

The Lab Depot, Inc. Plasticware. (2007). pp. 1-4. <http://www.labdepotinc.com/c-53-plastic-lab-containers.php>.*
PubChem. National Center for Biotechnology Information. PubChem Compound Database; CID=5793, pp. 1-25. http://pubchem.ncbi.nlm.nih.gov/compound/5793 (accessed May 11, 2015).*
"Isotonic." Merriam-Webster.com. Merriam-Webster, n.d. Web. May 1, 2015. pp. 1-3. <http://www.merriam-webster.com/dictionary/isotonic>.*
Anaizi et al; "Stability of Ganciclovir in Extemporaneously Compounded Oral Liquids"; American Journal of Health-System Pharamcy; Sep. 1999, pp. 3, vol. 56, No. 1738-41; American Society of Health System Pharmacists, United States of America.

* cited by examiner

*Primary Examiner* — James O Wilson
*Assistant Examiner* — Laura Daniel
(74) *Attorney, Agent, or Firm* — Thorpe North & Western, LLP

(57) ABSTRACT

Gancyclovir formulations that are ready-to-use, substantially particulate free, and stable upon storage are disclosed. Methods of manufacture and administration of such compositions are also provided.

19 Claims, No Drawings

GANCICLOVIR COMPOSITIONS AND RELATED METHODS

PRIORITY DATA

This application claims the benefit of U.S. Provisional Patent Application Ser. No. 61/872,625, filed Aug. 30, 2013, which is incorporated herein by reference.

FIELD OF THE INVENTION

The present invention relates to ganciclovir compositions and related methods. Accordingly, the present invention involves the fields of pharmacy, medicine, and chemistry.

BACKGROUND

Ganciclovir is an antiviral compound that has been used in the United States as well as several other countries for years. Liquid ganciclovir for oral administration has been known to be made from a powder of ganciclovir taken from a capsule and prepared to a concentration of 100 mg/ml of ganciclovir at a pH of 4.5. See, Am. J. Health Sys. Pharmacy, September 1999, vol 56, 1738-41. Additionally, an ophthalmic gel composition with ganciclovir has been described in which the concentration was about 0.15% and had a pH of about 7.4. Parenteral compositions of ganciclovir and its salts are described in U.S. Pat. No. 4,355,032. One parenteral composition that is currently being used is a lyophilized powder product of ganciclovir salt, namely ganciclovir sodium, sold in the United States under the trade name Cytovene®. This lyophilized powder product, supplied in a glass vial, requires reconstitution and dilution prior to administration to a patient.

There are at least three perceived drawbacks with the current lyophilized product: a) the lyophilization process is expensive, increasing the manufacturing cost per vial on an industrial scale; b) the reconstitution and dilution requires aseptic technique on the part of the health care giver, which could lead to occasional sterility compromise; and c) the product has a pH of about 11, which is not acceptable for some patients due to injection site reactions.

SUMMARY

Invention embodiments provide stable, injectable, and ready to administer aqueous ganciclovir compositions. In one embodiment, such compositions can be provided as a parental dosage form for parenteral administration to a subject.

In another aspect, such a composition may comprise or consist essentially of a ganciclovir base at a concentration of about 2.0 mg/ml, either sodium chloride or dextrose as a tonicity agent at a concentration sufficient to make the composition isotonic, and a pH adjuster to adjust the pH of the composition from about 5.5 to about 8, wherein the composition is terminally sterilized.

In another aspect, one or all of the composition invention embodiments are sterile, stable, and/or substantially particulate-matter-free. In another aspect, one or all of the compositions invention embodiments are stable. For example, in addition to being particulate-matter-free, the compositions can retain at least 95% or at least 99% of the original amount of ganciclovir after having been stored at about 60° C. for about one week.

Additionally provided is a container including a terminally sterilized stable ready-to-administer ganciclovir injectable composition consisting essentially of a ganciclovir base, at a concentration of about 2.0 mg/ml, either sodium chloride or dextrose as a tonicity agent at a concentration sufficient to make the composition isotonic, and a pH adjuster to adjust the pH of the composition from about 5.5 to about 8, wherein the container size ranges from about 50 ml to 1000 ml.

In addition to the compositions, dosage forms, and containers recited herein, the present invention encompasses methods of manufacturing the ganciclovir compositions and dosage forms recited herein. In one aspect, such a method may comprise: dissolving the ganciclovir base in water; adding a tonicity agent; optionally adjusting the pH of the solution; filling the composition into a container that facilitates ready to administration; and sterilizing said container. In another embodiment, the tonicity agent can be added first to water followed by the ganciclovir base. In a further embodiment, the tonicity agent can be added to water simultaneously with the ganciclovir base.

In additional embodiments, one or more of the above-recited compositions of the present invention are administered to subjects in need thereof for ganciclovir administration.

EXAMPLE EMBODIMENTS

Before the present invention is disclosed and described, it is to be understood that the invention embodiments are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a container" includes one or more of such containers and reference to "the agent" includes reference to one or more of such agents.

In describing and claiming the present invention, the following terminology will be used in accordance with the definitions set forth below.

As used herein, "ganciclovir" refers to a synthetic analogue of 2'-deoxy-guanosine with the general formula of (9-(1,3-dihydroxy-2-propoxymethyl)guanine). Ganciclovir has antiviral properties and can be used to treat or prevent cytomegalovirus (CMV) infections among others. Ganciclovir and various salts and prodrugs are currently indicated for a number of conditions including sight-threatening CMV retinitis in severely immunocompromised individuals, CMV pneumonitis in bone marrow transplant recipients, prevention of CMV disease in bone marrow and solid organ transplant recipients, as well as others. Where indicated, ganciclovir salts, prodrugs, and derivatives are recited as such herein.

As used herein, "subject" refers to a mammal. Examples of subjects include humans, and may also include other animals such as horses, pigs, cattle, dogs, cats, rats, rabbits, and aquatic mammals.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context, which one of skill in the art would be familiar with.

To clarify, a composition that is "substantially free of" an ingredient or element may still actually contain such ingredient or element but that ingredient or element is not intended to exert its function to its fullest extent.

As used herein, the term "ganciclovir base" refers to ganciclovir that is substantially free of its salt form. For example, in one aspect, greater than 50% of the active drug present in the composition is ganciclovir in its unsalted form. In another aspect, the unsalted form is greater than 60%, or greater than 80%, or greater than 90%, or greater than 95%, or greater than 98%, or greater than 99%.

As used herein, the term "particulate-matter-free" or its grammatical equivalents such as "particle free" refer to the state in which the composition of the present invention meets the USP requirements for particulate matter in parenteral solutions. See for example, USP XXXII, Chapter 788. One of skill in the art understands and knows how to assess whether a given composition meets USP particulate matter requirements.

As used herein, the term "about" is synonymous with "approximately" and is used to provide flexibility to a numerical value or range endpoint by providing that a given value may be "a little above" or "a little below" the value stated. However, it is to be understood that even when a numerical value is accompanied by the term "about" in this specification, that express support shall be provided at least for the exact numerical value as well as though the term "about" were not present.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa. In essence, use of one of these terms in the specification provides support for all of the others.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

In one invention embodiment, a non-lyophilized ganciclovir composition that is ready to administer to a patient or subject is provided. In another invention embodiment an injectable composition of ganciclovir that has a pH of less than about 11, or preferably from about 5 to about 9 is provided. In yet another invention embodiment, a ganciclovir injectable composition that is sterilized using steam or super-heated water is provided. In yet another aspect, an aqueous ganciclovir ready to administer parenteral composition that is prepared by aseptic sterilization is provided.

It has been surprisingly discovered that ganciclovir base provides acceptable solubility and stability in an aqueous injectable formulation compared to ganciclovir salts such as its sodium salt.

Ganciclovir sodium salt has previously been used because it is very soluble in water and thus creates no solubility issues for the formulation. However, ganciclovir sodium is not sufficiently stable in an aqueous formulation to permit prolonged shelf-storage. By contrast, ganciclovir base has limited solubility in water, thereby creating solubility issues for an injectable formulation. The present inventors have discovered that an aqueous solution of ganciclovir base when used at concentrations of about or below about 3 mg/ml is stable for extended shelf-storage, is free or substantially free of particulate matter, retains at least 95% of initial concentration of ganciclovir under accelerated storage or stability testing conditions, and can be terminally sterilized and thus provided in a ready to administer presentation or form for ease of use in a clinical setting, and at a more tolerable pH of less than 11 for increased patient comfort. Invention embodiments therefore provide a ganciclovir ready to administer injectable formulation and/or dosage form that has not been possible, or at least not thought possible, up to now.

To further emphasize this point, the present inventors affirmatively state that to the best of their knowledge and believe, it was not previously known or possible that a ready to use ganciclovir injectable composition could be terminally sterilized and commercially produced in non-lyophilized formulation for commercial distribution. This discovery was unexpected at least in part, because the currently approved commercial product is a lyophilized aseptically manufactured product.

An additional advantage provided by the present formulations is the reduction of pH. Rather than a high pH, such as the pH of 11 as in the currently approved ganciclovir product, the present compositions have a lower pH value such as about 9, or about 8, or about 7, or about 6, or about 5, or any ranges or subranges encompassing these values (e.g., 5-6, 5-8, 5-9, 7-9, 8-9, 6-9, etc.). In some aspects, the pH may be from about 5 to about 9. A pH adjuster may not be needed, if the desired pH is about 5.0 to about 7.0, or about 5.0 to about 6.5.

Terminal sterilization can be accomplished in a suitable sterilizer employing steam, supersaturated water, or a combination thereof (generally known as heat sterilization). Appropriate sterilization conditions can be determined based on the number of units and the size of the units to be sterilized. In one aspect, sterilization is conducted in an air over-pressure type sterilizer or steam sterilizer or water cascade type sterilizer, several of which are commercially available. Exemplary time and temperature levels required for adequate sterilization is to achieve and maintain a temperature of at least about 121 degrees ° C. for from about 7-8 minutes to about 30 minutes or more as needed.

It should be recognized that even though the current compositions are terminally sterilizable, under certain conditions, the compositions may be sterilized aseptically. Such aseptic sterilization may include filtration or radiation methods, which are well-known in the art.

The present formulations can, in some embodiments, include a tonicity agent. Suitable tonicity agents may be selected from a number of tonicity agents. Exemplary agents include without limitation: sodium chloride, mannitol, sorbitol, dextrose, or organic solvents such as ethanol, glycerin, sorbitol, propylene glycol, etc., or a combination thereof. The amount of tonicity agent in a given formulation can be selected based on the nature of the tonicity agent and the tonicity of the composition without the tonicity agent. In one embodiment, an isotonic solution can have an osmotic pressure of about 250-350 mOsmol/Kg. One of skill in the art is well aware of how to make a solution isotonic. See for example, Remington: The Science and Practice of Pharmacy, Chapter 18, 21$^{st}$ Edition, David B. Troy, Editor, Lippincott, Williams & Wikins 2006, which is incorporated by reference herein.

In one embodiment, the pH of the compositions of the present invention may be unadjusted, in which case, it may be about 5.5. In embodiments where the pH is to be adjusted, a suitable pH adjuster such as sodium hydroxide, potassium hydroxide, hydrochloric acid, sulfuric acid, or organic pH adjustors such as cysteine, lysine, acetic acid, citric acid, ascorbic acid, salicylic acid, or others may be used.

An appropriate concentration of acid or base may be in some embodiments, from about 0.1M to 1M or more. The ready to use compositions of the present invention may be supplied in a glass vial (for example, Type II) or in a plastic container made from polyethylene, polypropylene or a combination thereof. The container may range in size from about 10 ml to about 500 ml or more if needed. In another aspect, the container size may range from about 50 to 1000 ml. In one specific aspect, the container is about 250 ml.

In another embodiment, methods are provided for treating a subject in need thereof with an antiviral composition of ganciclovir in a stable, injectable, ready to administer, sterile particulate-matter-free aqueous composition consisting essentially of a ganciclovir base at a concentration of from about 1 mg/ml to about 3 mg/ml;

a tonicity agent in sufficient concentration to make the composition isotonic; and optionally a pH adjuster, wherein the composition has a pH of from about 5 to about 9 a ganciclovir base at a concentration of from about 1 mg/ml to about 3 mg/ml;

a tonicity agent in sufficient concentration to make the composition isotonic; and optionally a pH adjuster, wherein the composition has a pH of from about 5 to about 9.

In other embodiments, any of the above-recited ganciclovir compositions of the present invention is suitably administered to treat a subject that is in need thereof.

Examples

Exemplary formulations of the present invention are shown in Tables 1 and 2 as follows:

TABLE 1

Composition of Formulations 1-4

| Ingredients | Formulation 1 | Formulation 2 | Formulation 3 | Formulation 4 |
| --- | --- | --- | --- | --- |
| Ganciclovir | 2 mg/mL | 2 mg/mL | 2 mg/mL | 2 mg/mL |
| Sodium chloride | 8 mg/mL | — | — | — |
| Dextrose | — | 40 mg/mL | — | — |
| Propylene glycol | — | — | 25 mg/mL | — |
| Mannitol | — | — | — | 40 mg/mL |
| NaOH to adjust pH to | 7.5 | 5.9 (not adjusted) | 7.5 | 7.5 |
| Water for Injection | q.s. | q.s. | q.s. | q.s. |

TABLE 2

Composition of Formulations 5-8

| Ingredients | Formulation 5 | Formulation 6 | Formulation 7 | Formulation 8 |
|---|---|---|---|---|
| Ganciclovir | 2 mg/mL | 2 mg/mL | 2.5 mg/mL | 1.5 mg/mL |
| Sodium chloride | — | — | — | 9 mg/mL |
| Dextrose | — | 45 mg/mL | 45 mg/mL | — |
| Glycerol | 25 mg/mL | — | — | — |
| NaOH to adjust pH to | 7.5 | 5.8 (not adjusted) | 7.5 | 7.5 |
| Water for Injection | q.s. | q.s. | q.s. | q.s. |

General Procedure:

Ready to use formulations are prepared in the following general manner. Gancyclovir is weighed and dissolved in warm water for injection. To the solution, the tonicity agent is added and dissolved. If required, the pH of the solution is adjusted with NaOH. The solution is filtered, filled into flexible polypropylene containers and steam sterilized in an autoclave at a temperature of about 121° C. for a duration of about 15-30 minutes.

It is to be understood that the above-described arrangements are only illustrative of the application of the principles of the present invention. Numerous modifications and alternative but equivalent arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A stable, injectable, ready to administer, sterile, particulate-matter-free, aqueous ganciclovir composition consisting essentially of:
    a ganciclovir base at a concentration of from 1 mg/ml to 3 mg/ml;
    a tonicity agent; and
    optionally a pH adjuster,
wherein the composition has a pH of from 5 to 9 and the composition has an osmotic pressure of 250-350 mOsmol/Kg.

2. The composition of claim 1, wherein the ganciclovir is present in an amount of from 1.5 mg/ml to 2.5 mg/ml.

3. The composition of claim 2, wherein the ganciclovir is present in an amount of 2 mg/ml.

4. The composition of claim 1, wherein the tonicity agent is a member selected from the group consisting of: sodium chloride, mannitol, sorbitol, dextrose, ethanol, glycerin, sorbitol, propylene glycol, and combinations thereof.

5. The composition of claim 4, wherein the tonicity agent is sodium chloride.

6. The composition of claim 1, wherein the pH of the composition is 7.5.

7. The composition of claim 1, wherein the pH adjuster is selected from the group consisting of: sodium hydroxide, potassium hydroxide, hydrochloric acid, sulfuric acid, cysteine, lysine, acetic acid, citric acid, ascorbic acid, salicylic acid, and combinations thereof.

8. The composition of claim 1, wherein the pH adjuster is sodium hydroxide.

9. The composition of claim 1, wherein the composition does not include a pH adjuster and the composition has a pH of from 5.5 to 5.8.

10. A stable, injectable, ready to administer, sterile, particulate-matter-free, aqueous ganciclovir composition, consisting essentially of:
    a ganciclovir base at a concentration of 2.0 mg/ml;
    sodium chloride or dextrose as a tonicity agent; and
    a pH adjuster to adjust the pH of the composition to from 5.5 to 8,
wherein the composition is terminally sterilized and the composition has an osmotic pressure of 250-350 mOsmol/Kg.

11. The composition of claim 10, wherein the tonicity agent is sodium chloride.

12. The composition of claim 10, wherein the tonicity agent is dextrose.

13. The composition of claim 10, wherein the pH is 7.5.

14. The composition of claim 10, wherein the pH adjuster is selected from the group consisting of: sodium hydroxide, potassium hydroxide, hydrochloric acid, sulfuric acid, cysteine, lysine, acetic acid, citric acid, ascorbic acid, salicylic acid, and combinations thereof.

15. A container comprising a stable ready to administer ganciclovir injectable composition consisting essentially of:
    a ganciclovir base, at a concentration of 2.0 mg/ml;
    sodium chloride or dextrose as a tonicity agent; and
    a pH adjuster to adjust the pH of the composition to from 5.5 to 8,
wherein the composition has an osmotic pressure of 250-350 mOsmol/Kg and the container size ranges from 50 ml to 1000 ml.

16. The container of claim 15, wherein the composition is terminally sterilized.

17. The container of claim 15, wherein the container is made from a material comprising polyethylene or polypropylene or a combination thereof.

18. A method of manufacturing an aqueous, stable, injectable, ready to administer, ganciclovir composition consisting essentially of a ganciclovir base, at a concentration of from 1 mg/ml to 3 mg/ml, a tonicity agent, and optionally a pH adjuster, wherein the composition has a pH from 5 to 9, wherein the composition is free of particulate matter and the composition has an osmotic pressure of 250-350 mOsmol/Kg, comprising:
    dissolving the ganciclovir base in water;
    adding a tonicity agent;
    optionally adjusting the pH of the composition;
    filling the composition into a container; and
    sterilizing said container.

19. The method of claim 18, wherein the tonicity agent is added to water either prior to or simultaneously with the ganciclovir base.

* * * * *